US010709871B2

(12) United States Patent
Ducharme et al.

(10) Patent No.: US 10,709,871 B2
(45) Date of Patent: Jul. 14, 2020

(54) CATHETER HAVING A STEERABLE TIP

(71) Applicant: Novasentis, Inc., Burlingame, CA (US)

(72) Inventors: Richard Ducharme, Alexandria, PA (US); Mark Levatich, State College, PA (US); Christophe Ramstein, San Francisco, CA (US)

(73) Assignee: Strategic Polymer Sciences, Inc., State College, PA (US)

( * ) Notice: Subject to any disclaimer, the term of this patent is extended or adjusted under 35 U.S.C. 154(b) by 0 days.

(21) Appl. No.: 15/832,617

(22) Filed: Dec. 5, 2017

(65) Prior Publication Data

US 2018/0099121 A1    Apr. 12, 2018

Related U.S. Application Data

(62) Division of application No. 14/015,841, filed on Aug. 30, 2013, now Pat. No. 9,833,596.

(51) Int. Cl.
*A61M 25/01*    (2006.01)
*A61M 25/00*    (2006.01)
(Continued)

(52) U.S. Cl.
CPC .... *A61M 25/0158* (2013.01); *A61M 25/0009* (2013.01); *A61B 1/0051* (2013.01);
(Continued)

(58) Field of Classification Search
CPC .......... A61M 25/0133; A61M 25/0158; A61M 25/01; A61M 2025/0166; A61B 18/1492; A61B 1/0051; A61B 1/0058
See application file for complete search history.

(56) References Cited

U.S. PATENT DOCUMENTS 4,863,442 A    9/1989 DeMello et al.
5,234,416 A    8/1993 Macaulay et al.
(Continued)

FOREIGN PATENT DOCUMENTS

JP    2010283926 A    12/2010
JP    2011172339 A    9/2011
(Continued)

OTHER PUBLICATIONS

Non-Final Rejection issued in U.S. Appl. No. 14/015,841, dated Jun. 19, 2015.
(Continued)

*Primary Examiner* — Nilay J Shah
(74) *Attorney, Agent, or Firm* — Hogan Lovells US LLP

(57) ABSTRACT

A catheter includes an electromechanical polymer (EMP) actuator disposed in a steerable tip at the distal end of the catheter. When activated, the EMP actuator deflects the steerable tip through an angle between 0 and 270 degrees, thus permitting the operator to steer the steerable tip through the vasculature. The steerable tip also has at least a first relatively stiff region and a second relatively flexible region, and the EMP actuator is provided next to the first relatively stiff region so that the steerable tip may toward the flexible region when activated. In one implementation, an external interface allows a user to select by name one of many sets of control signals, with each set of control signals being signals calibrated for configuring the catheter to mimic a known catheter.

13 Claims, 12 Drawing Sheets

(51) Int. Cl.
*A61B 18/14* (2006.01)
*A61B 1/005* (2006.01)

(52) U.S. Cl.
CPC .. *A61B 18/1492* (2013.01); *A61M 2025/0058* (2013.01); *Y10T 29/49117* (2015.01)

(56) References Cited

U.S. PATENT DOCUMENTS

| | | | |
|---|---|---|---|
| 5,254,107 A | 10/1993 | Soltesz | |
| 5,263,876 A | 11/1993 | Johnescu et al. | |
| 5,350,966 A | 9/1994 | Culp | |
| 5,469,734 A * | 11/1995 | Schuman | G01Q 40/00 310/317 |
| 5,519,278 A | 5/1996 | Kahn et al. | |
| 5,531,685 A * | 7/1996 | Hemmer | A61M 25/0158 604/531 |
| 5,588,964 A | 12/1996 | Imran et al. | |
| 5,681,336 A * | 10/1997 | Clement | A61B 17/320758 604/96.01 |
| 6,007,478 A | 12/1999 | Siess | |
| 6,071,234 A | 6/2000 | Takada | |
| 6,144,547 A | 11/2000 | Retseptor | |
| 6,160,084 A | 12/2000 | Langer et al. | |
| 6,183,435 B1 | 2/2001 | Bumbalough et al. | |
| 6,278,084 B1 | 8/2001 | Maynard | |
| 6,376,971 B1 | 4/2002 | Pelrine et al. | |
| 6,385,472 B1 | 5/2002 | Hall et al. | |
| 6,423,412 B1 | 7/2002 | Zhang et al. | |
| 6,514,237 B1 | 2/2003 | Maseda | |
| 6,605,246 B2 | 8/2003 | Zhang et al. | |
| 6,703,257 B2 | 3/2004 | Takeuchi et al. | |
| 6,770,081 B1 | 8/2004 | Cooper et al. | |
| 6,787,238 B2 | 9/2004 | Zhang et al. | |
| 6,809,462 B2 | 10/2004 | Pelrine et al. | |
| 6,812,624 B1 | 11/2004 | Pei et al. | |
| 6,852,416 B2 | 2/2005 | Zhang et al. | |
| 6,877,325 B1 | 4/2005 | Lawless | |
| 6,888,291 B2 | 5/2005 | Arbogast et al. | |
| 6,891,317 B2 | 5/2005 | Pei et al. | |
| 6,921,360 B2 | 7/2005 | Banik | |
| 6,939,338 B2 | 9/2005 | Waldhauser et al. | |
| 6,969,395 B2 | 11/2005 | Eskuri | |
| 6,979,312 B2 | 12/2005 | Shimada | |
| 6,997,870 B2 | 2/2006 | Couvillon, Jr. | |
| 7,038,357 B2 | 5/2006 | Goldenberg et al. | |
| 7,078,101 B1 | 7/2006 | Ramotowski et al. | |
| 7,097,615 B2 | 8/2006 | Banik et al. | |
| 7,128,707 B2 | 10/2006 | Banik | |
| 7,199,501 B2 | 4/2007 | Pei et al. | |
| 7,224,106 B2 | 5/2007 | Pei et al. | |
| 7,261,686 B2 | 8/2007 | Couvillon, Jr. | |
| 7,339,572 B2 | 3/2008 | Schena | |
| 7,368,862 B2 | 5/2008 | Pelrine et al. | |
| 7,567,681 B2 | 7/2009 | Pelrine et al. | |
| 7,766,896 B2 | 8/2010 | Kornkven Volk et al. | |
| 7,839,647 B2 | 11/2010 | Lee et al. | |
| 7,909,844 B2 | 3/2011 | Alkhatib et al. | |
| 7,944,735 B2 | 5/2011 | Bertin et al. | |
| 7,952,261 B2 | 5/2011 | Lipton et al. | |
| 7,971,850 B2 | 7/2011 | Heim et al. | |
| 8,126,534 B2 | 2/2012 | Maschke | |
| 8,222,799 B2 | 7/2012 | Polyakov et al. | |
| 8,362,882 B2 | 1/2013 | Heubel et al. | |
| 8,384,271 B2 | 2/2013 | Kwon et al. | |
| 8,390,594 B2 | 3/2013 | Modarres et al. | |
| 8,398,693 B2 | 3/2013 | Weber et al. | |
| 8,414,632 B2 | 4/2013 | Kornkven Volk et al. | |
| 8,427,441 B2 | 4/2013 | Paleczny et al. | |
| 8,564,181 B2 | 10/2013 | Choi et al. | |
| 2001/0051769 A1 | 12/2001 | Hoek et al. | |
| 2003/0006669 A1 * | 1/2003 | Pei | A61M 5/142 310/309 |
| 2003/0065373 A1 | 4/2003 | Lovett et al. | |
| 2003/0236445 A1 * | 12/2003 | Couvillon, Jr. | A61M 25/0105 600/114 |
| 2004/0138733 A1 | 7/2004 | Weber et al. | |
| 2004/0217671 A1 * | 11/2004 | Rosenthal | A61M 5/142 310/328 |
| 2006/0025809 A1 | 2/2006 | Shelton, IV | |
| 2006/0047302 A1 | 3/2006 | Ortiz et al. | |
| 2006/0064055 A1 | 3/2006 | Pile-Spellman et al. | |
| 2006/0129130 A1 | 6/2006 | Tal et al. | |
| 2006/0293643 A1 | 12/2006 | Wallace et al. | |
| 2007/0032851 A1 | 2/2007 | Shippy, III et al. | |
| 2007/0043338 A1 | 2/2007 | Moll et al. | |
| 2007/0060997 A1 | 3/2007 | de Boer | |
| 2007/0123750 A1 | 5/2007 | Baumgartner et al. | |
| 2007/0152974 A1 | 7/2007 | Kim et al. | |
| 2007/0200467 A1 | 8/2007 | Heydt et al. | |
| 2008/0228167 A1 * | 9/2008 | Mittermeyer | A61B 5/031 604/523 |
| 2008/0284277 A1 | 11/2008 | Kwon et al. | |
| 2009/0002205 A1 | 1/2009 | Klinghult et al. | |
| 2009/0002328 A1 | 1/2009 | Ullrich et al. | |
| 2010/0079264 A1 | 4/2010 | Hoellwarth | |
| 2010/0090813 A1 | 4/2010 | Je et al. | |
| 2010/0316242 A1 | 12/2010 | Cohen et al. | |
| 2011/0038625 A1 | 2/2011 | Zellers et al. | |
| 2011/0133598 A1 | 6/2011 | Jenninger et al. | |
| 2011/0290686 A1 | 12/2011 | Huang | |
| 2012/0017703 A1 | 1/2012 | Ikebe et al. | |
| 2012/0105333 A1 | 5/2012 | Maschmeyer et al. | |
| 2012/0121944 A1 | 5/2012 | Yamamoto et al. | |
| 2012/0126663 A1 | 5/2012 | Jenninger et al. | |
| 2012/0126959 A1 | 5/2012 | Zarrabi et al. | |
| 2012/0128960 A1 | 5/2012 | Busgen et al. | |
| 2012/0178880 A1 | 7/2012 | Zhang et al. | |
| 2012/0194448 A1 | 8/2012 | Rothkopf | |
| 2012/0206248 A1 | 8/2012 | Biggs | |
| 2012/0223880 A1 | 9/2012 | Birnbaum et al. | |
| 2012/0239032 A1 | 9/2012 | Zhang et al. | |
| 2013/0123692 A1 | 5/2013 | Zhang et al. | |
| 2013/0207793 A1 | 8/2013 | Weaber et al. | |
| 2014/0035735 A1 | 2/2014 | Zellers et al. | |
| 2014/0085065 A1 | 3/2014 | Biggs et al. | |
| 2014/0090424 A1 | 4/2014 | Charbonneau et al. | |
| 2014/0139328 A1 | 5/2014 | Zellers et al. | |
| 2014/0139329 A1 | 5/2014 | Ramstein et al. | |
| 2014/0139436 A1 | 5/2014 | Ramstein et al. | |
| 2014/0140551 A1 | 5/2014 | Ramstein | |
| 2014/0191973 A1 | 7/2014 | Zellers et al. | |

FOREIGN PATENT DOCUMENTS

| | | |
|---|---|---|
| JP | 2012134998 A | 7/2012 |
| KR | 20060107259 A | 10/2006 |
| KR | 20110110212 A | 10/2011 |
| KR | 20120013273 A | 2/2012 |
| KR | 20120063318 A | 6/2012 |
| KR | 20120078529 A | 7/2012 |
| KR | 20120105785 A | 9/2012 |
| WO | 2007102939 A1 | 9/2007 |
| WO | 2008016403 A1 | 2/2008 |
| WO | 2010/085575 A1 | 7/2010 |

OTHER PUBLICATIONS

PCT International Preliminary Report on Patentability for PCT/US2014/053494, dated Mar. 10, 2016, 10 pages.
Brochu, P. et al., "Advances in Dielectric Elastomers for Actuators and Artificial Muscles," Marcromolecular Journals, *Macromolecular Rapid Communications*, dated 2010, pp. 10-36.
Mazzoldi, A. et al., "Conductive polymer based structures for a steerable catheter," in *Smart Structures and Materials 2000: Electroactive Polymer Acuators and Devices (EAPAD)*, proceedings of SPIE vol. 3987 (2000), pp. 273-280.
Arai, F. et al., "Intelligent Assistance in Operation of Active Catheter for Minimum Invasive Surgery," paper for IEEE International Workshop on Robot and Human Communication, dated Jun. 1994, pp. 192-197.
Fukuda, T. et al., "Micro Active Catheter System with Multi Degrees of Freedom," paper for IEEE, dated 1994, pp. 2290-2295.

(56) References Cited

OTHER PUBLICATIONS

Guo, S. et al., "Micro Active Guide Wire Catheter System," paper for IEEE, dated Apr. 1995, pp. 172-177.
Della Santa, A. et al., "Intravascular Microcatheters Steered by Conducting Polymer Actuators," paper for IEEE, dated Jan. 1997, pp. 2203-2204.
Guo, S. et al., "Micro Active Catheter Using ICPF Actuator, Characteristic Evaluation, Electrical Model and Operability Evaluation," paper for IEEE, dated Jun. 1996, pp. 1312-1317.
Guo, S. et al., "Micro Active Guide Wire Catheter Using ICPF Actuator," paper for IEEE, dated Sep. 1996, pp. 729-734.
Guo, S. et al., "Micro Catheter System with Active Guide Wire," paper for IEEE International Conference on Robotics and Automation, dated Jun. 1995, pp. 79-84.
Bar-Cohen, Y., Biomimetics: Biologically Inspired Technologies, textbook Chapter 10, "Artificial Muscles Using Electroactive Polymers", 2005, Jet Propulsion Laboratory (JPL), Pasadena, CA, pp. 267-290.
Spinks, G. M. et al., "Strain Response from Polypyrrole Actuators under Load," *Advanced Functional Materials*, dated Jun. 2002, pp. 437-440.
PCT International Search Report and Written Opinion, dated Nov. 7, 2008, International Application No. PCT/US2008/070450, 10 pages.
Matysek, Marc et al., "Combined Driving and Sensing Circuitry for Dielectric Elastomer Acutuators in mobile applications", Electroactive Polymer Actuators and Devices (EAPAD) 2011, Proc. of SPIE vol. 7976, 797612, 11 pages.
Neese, Bret et al., "Large Electrocaloric Effect in Ferroelectric Polymers Near Room Temperature", Science vol. 321, Aug. 8, 2008, pp. 821-823.
Zhang Q. M. et al., "Giant Electrostriction and Relaxor Ferroelectrtic Behavior in Electron-Irradiated Poly(vinylidene fluoride-trifluoroethylene) Copolymer", Science vol. 280, Jun. 26, 1998, pp. 2101-2104.
Xia, F. et al., "High Electromechanical Responses in a Poly(vinylidene fluoride-trifluoroethylene-chlorofluoroethylene) Terpolymer", Advanced Materials, vol. 14, Issue 21, Nov. 2002, pp. 1574-1577.
PCT International Search Report and Written Opinion dated Dec. 23, 2013, International Application No. PCT/US2013/053594, 9 pages.
PCT International Search Report and Written Opinion dated Mar. 17, 2014, International Application No. PCT/US2013/071085, 10 pages.
PCT International Search Report and Written Opinion dated Mar. 13, 2014, International Application No. PCT/US2013/071072, 15 pages.
PCT International Search Report and Written Opinion dated Mar. 20, 2014, International Application No. PCT/US2013/071075, 12 pages.
PCT International Search Report and Written Opinion dated Mar. 28, 2014, International Application No. PCT/US2013/071078, 13 pages.
PCT International Search Report and Written Opinion dated Apr. 28, 2014, Internationai Application No. PCT/US2013/071062, 11 pages.
PCT International Preliminary Report on Patentability dated Jun. 4, 2015, International Application No. PCT/US2013/071072, 9 pages.
PCT International Preliminary Report on Patentability dated Jun. 4, 2015, International Application No. PCT/US2013/071075, 9 pages.
PCT International Preliminary Report on Patentability, dated Jun. 4, 2015, International Application No. PCT/US2013/071078, 10 pages.
PCT International Preliminary Report on Patentability, dated Jun. 4, 2015, International Application No. PCT/US2013/071085, 7 pages.
PCT International Preliminary Report on Patentability dated Jul. 16, 2015, International Application No. PCT/IB2013/003212, 15 pages.
PCT International Search Report and Written Opinion, dated Oct. 15, 2014, International Application No. PCT/IB2013/003212, 20 pages.
PCT International Search Report and Written Opinion, dated Dec. 18, 2014, International Application No. PCT/US2014/053494, 11 pages.
PCT International Preliminary Report on Patentability dated Jul. 16, 2015, International Application No. PCT/US2014/010219, 14 pages.
PCT International Search Report and Written Opinion, dated May 23, 2014, International Application No. PCT/US2014/010219, 21 pages.
Non-Final Rejection issued in U.S. Appl. No. 14/015,841, dated Feb. 18, 2016.
Final Rejection issued in U.S. Appl. No. 14/015,841, dated Aug. 1, 2016.
Non-Final Rejection issued in U.S. Appl. No. 14/015,841, dated Mar. 1, 2017.
Notice of Allowance issued in U.S. Appl. No. 14/015,841, dated Aug. 9, 2017.

\* cited by examiner

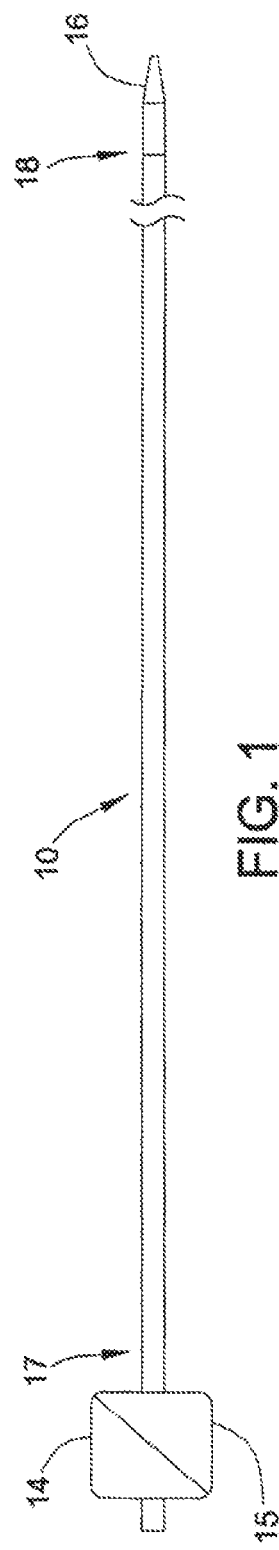
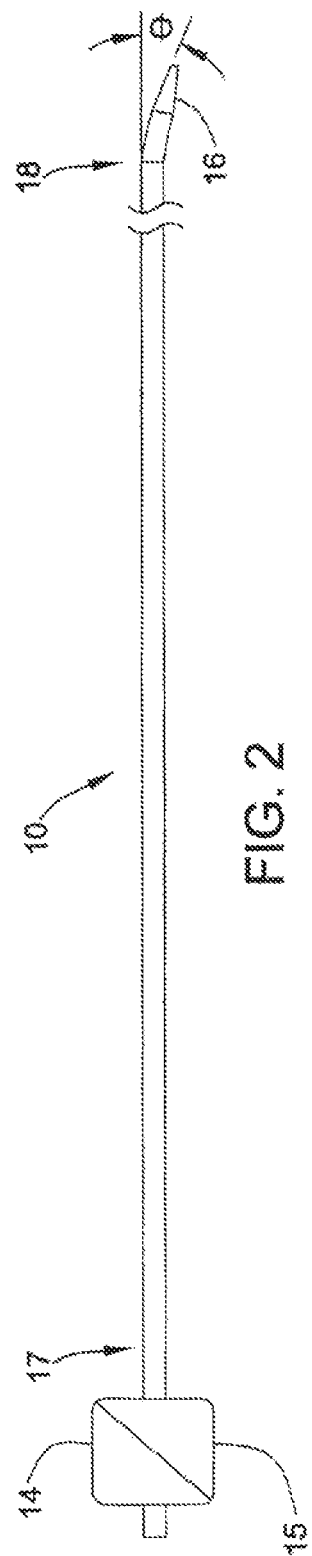
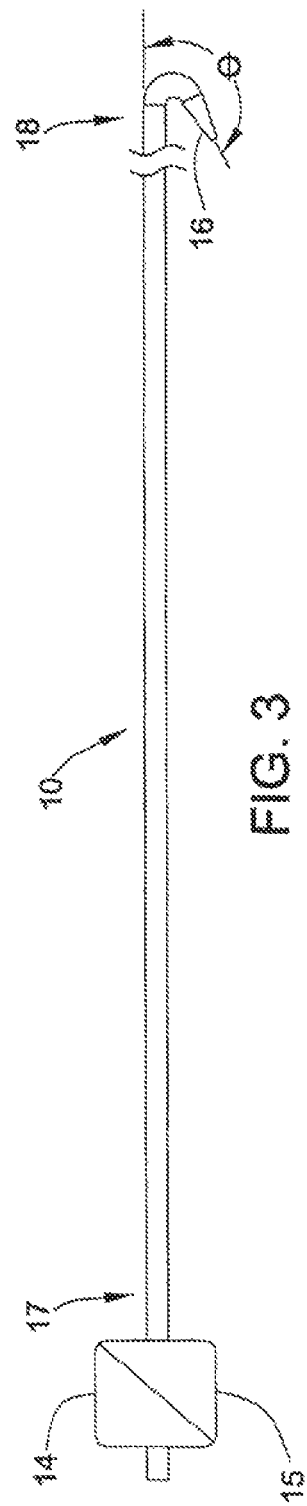

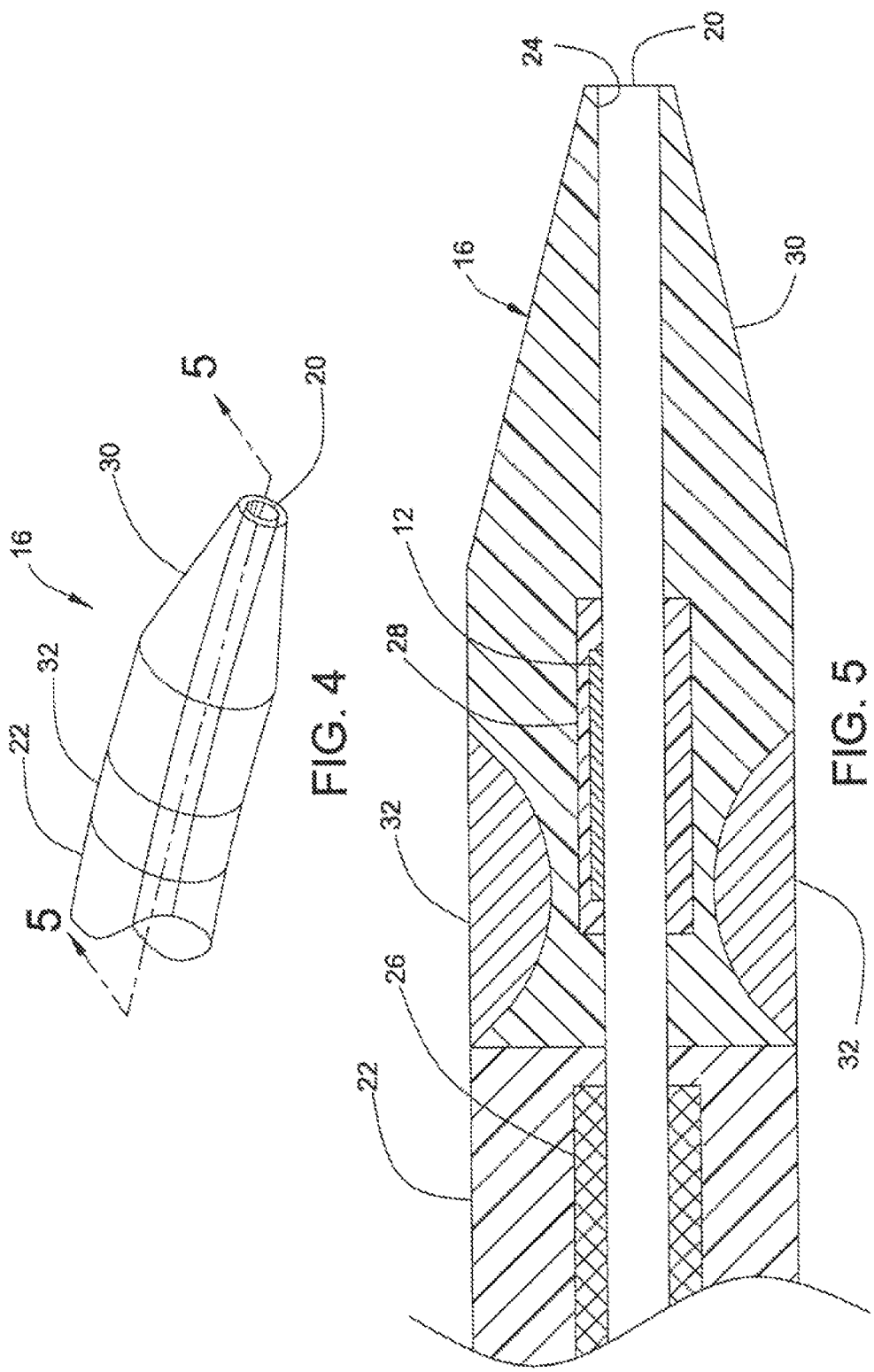

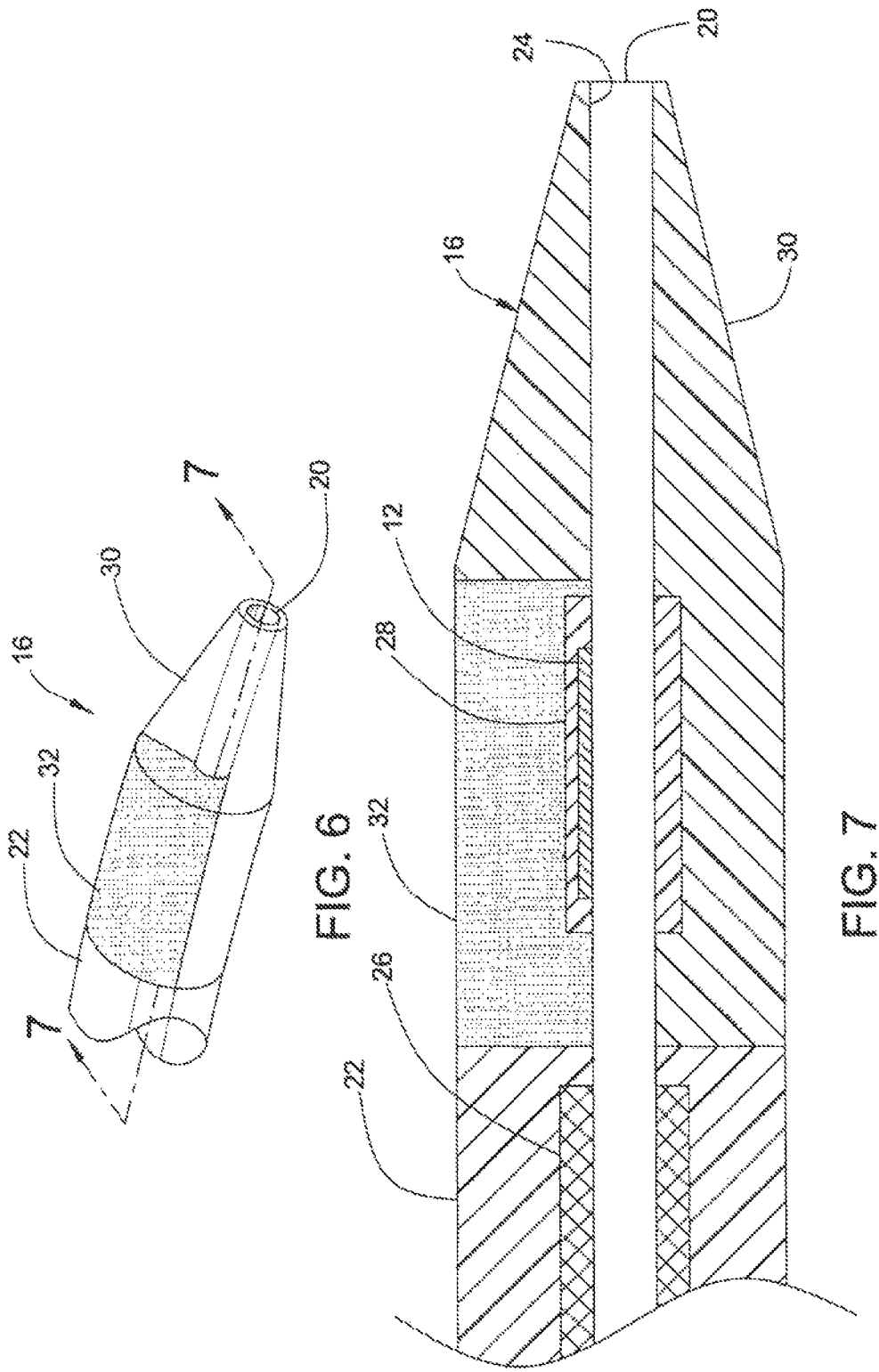

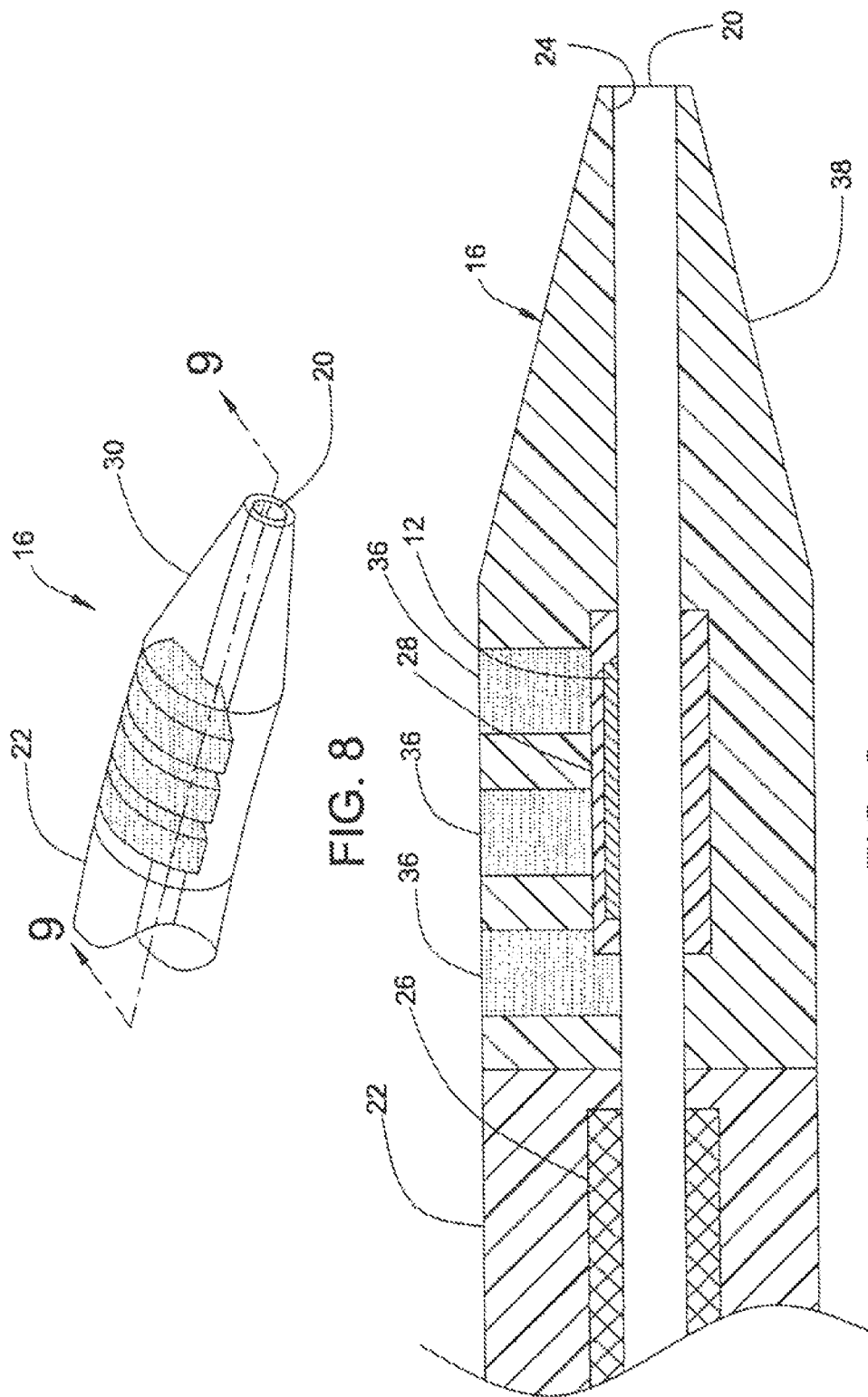

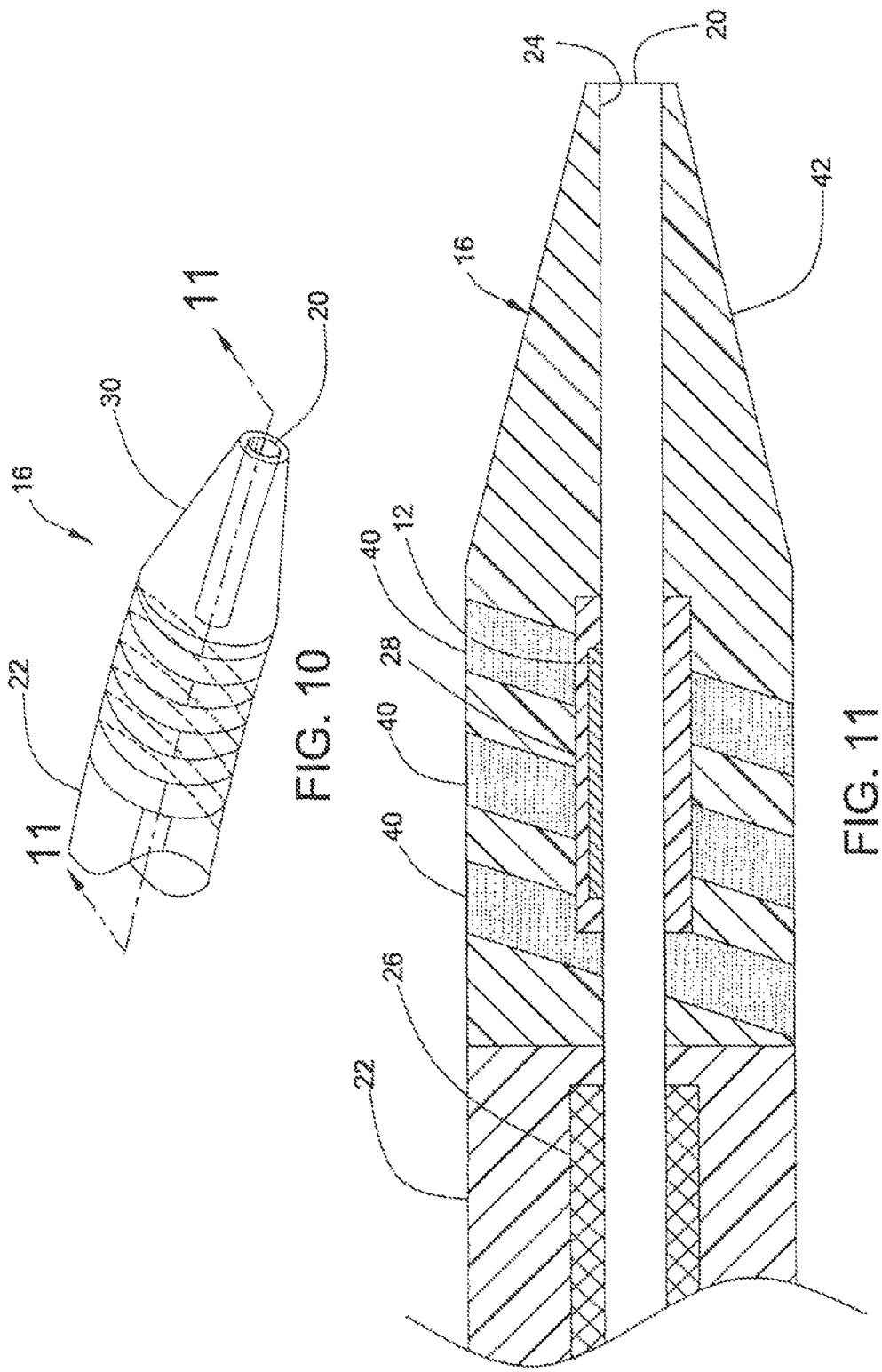

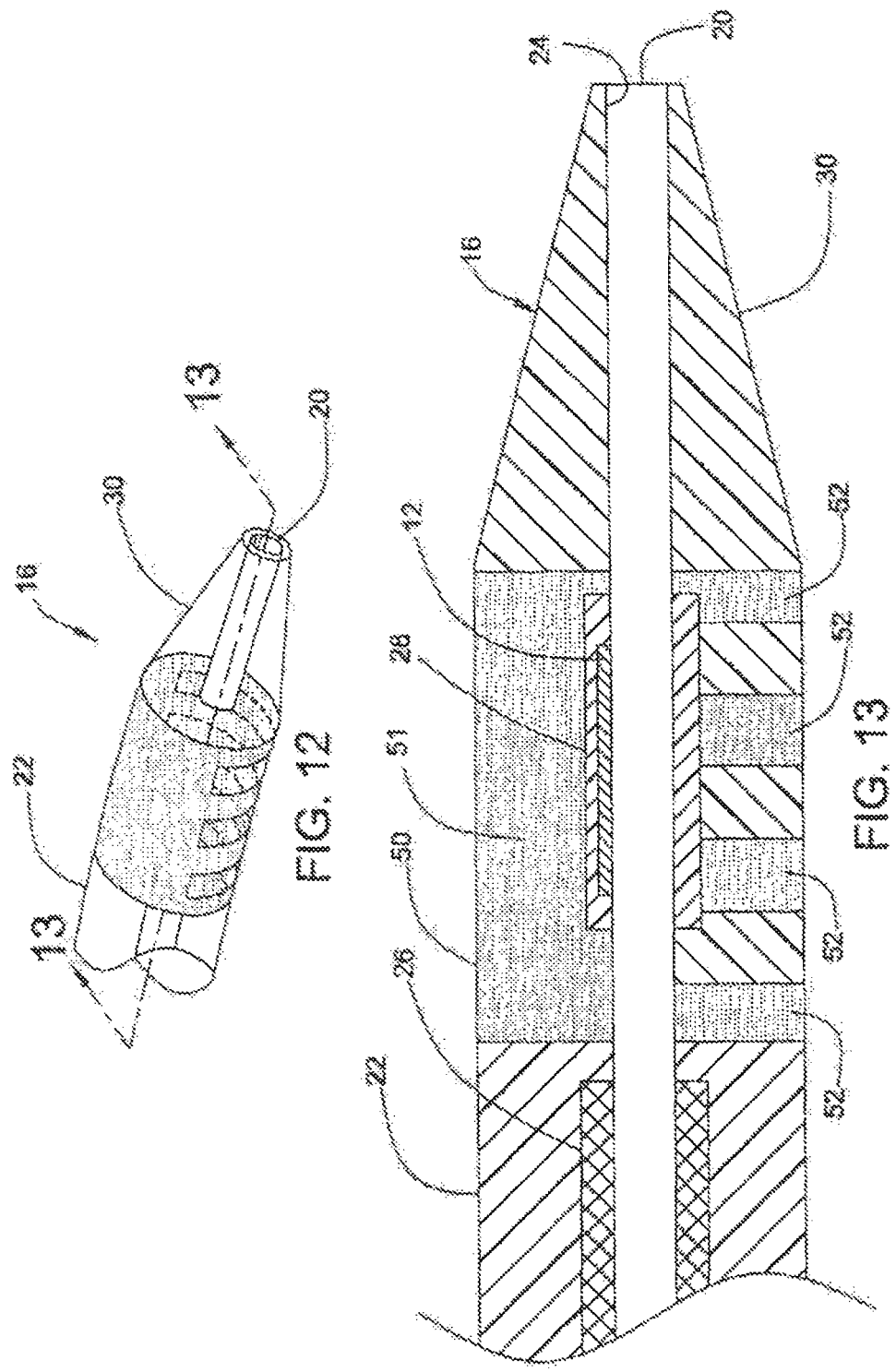

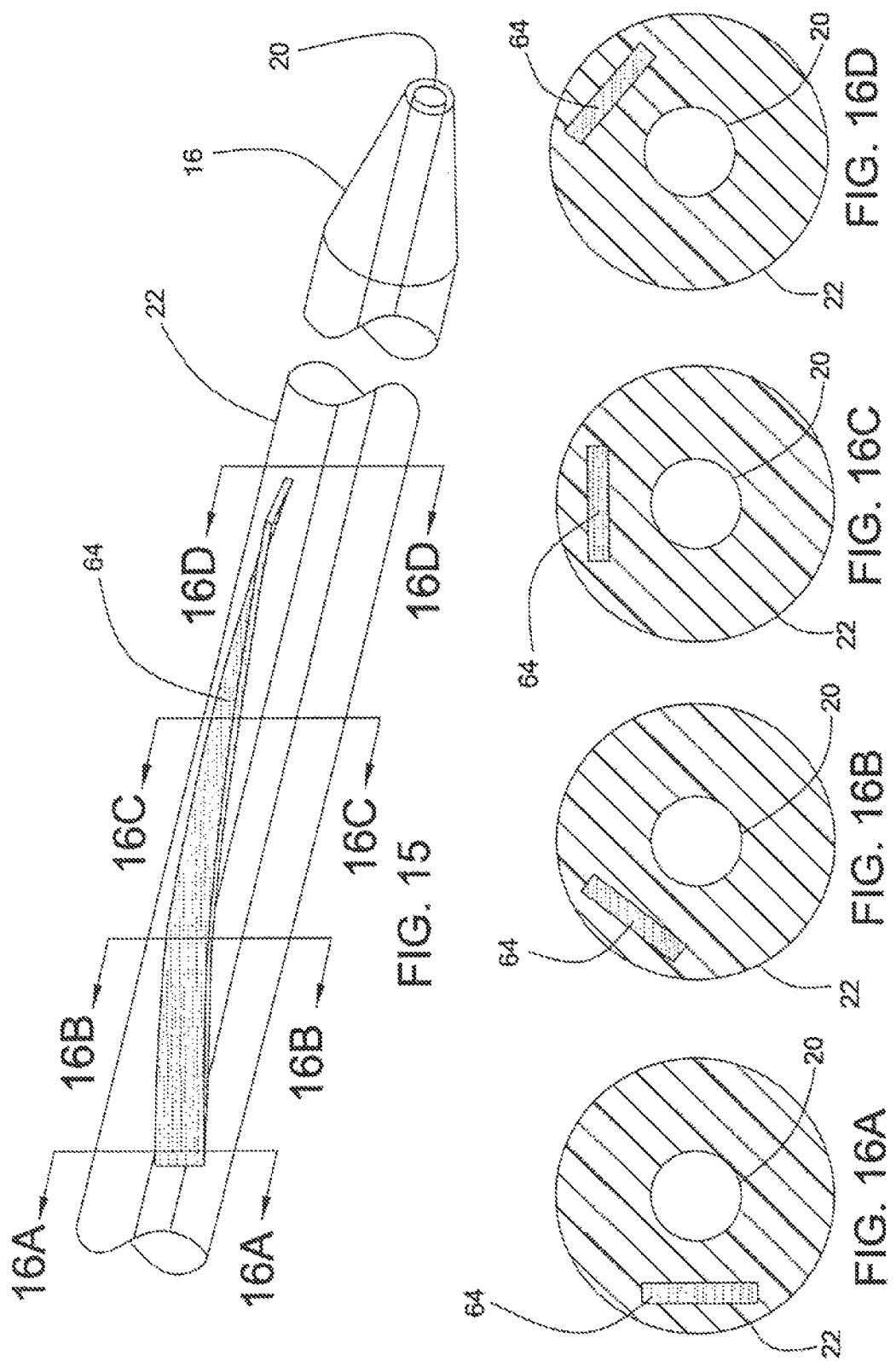

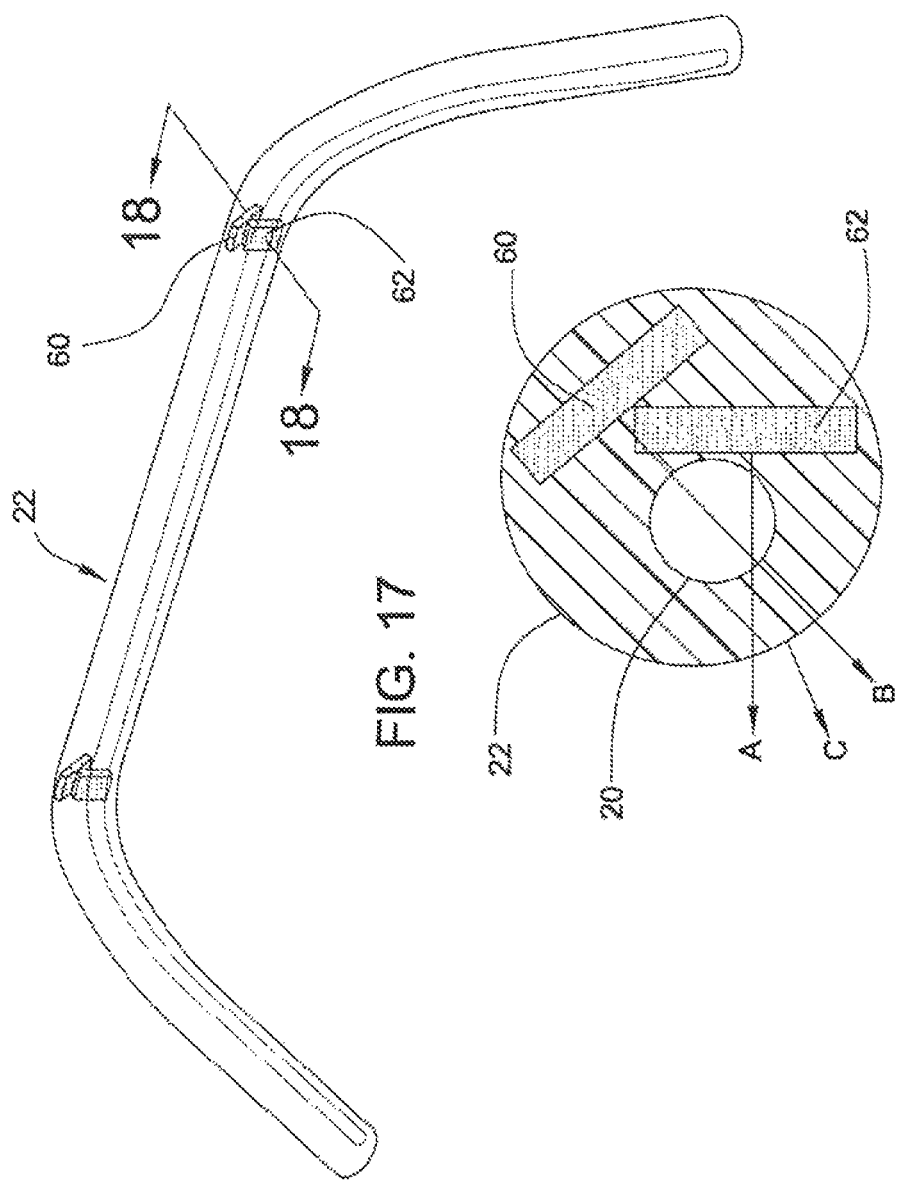

CATHETER HAVING A STEERABLE TIP

This application is a Divisional of allowed U.S. patent application Ser. No. 14/015,841, filed Aug. 30, 2013, entitled "CATHETER HAVING A STEERABLE TIP," which is incorporated herein by reference for all purposes.

BACKGROUND OF THE INVENTION

1. Field of the Invention

This invention relates generally to catheters and, more particularly, to catheters using electroactive or electromechanical polymer actuators to provide articulation.

2. Discussion of the Related Art

Numerous medical procedures (e.g., angioplasty, stenting, cardiac ablation, and vascular diagnostics) use catheters. It is difficult, however, to steer a catheter's tip to a desired location in the body effectively through the vasculature. Typically, a procedure begins when a physician inserts a distal portion of a guide wire into a patient's vasculature system. Once the distal portion of the catheter—which follows the distal portion of the guide wire—enters into the vasculature, the physician can no longer manipulate the distal portion of the guide wire directly. Thereafter, the physician must advance the guide wire through the vasculature by manipulating (e.g., pulling, pushing, and twisting motions) from the proximal end of the catheter. The typical guide wire relies on its flexibility to avoid causing trauma to the surrounding tissues. This flexibility makes steering the guide wire even more difficult.

Another drawback in conventional catheter use is that many procedures require multiple catheters. This is because, to reach an intended location within the vasculature, multiple catheter tips with different preformed shapes and different degrees of bending may be required. Consequently, the hospital must maintain a large inventory of catheters because it is difficult to predict in advance which catheters are required. The repeated catheter extraction and insertion may also increase the risks of infections and trauma to the patient.

U.S. patent application Ser. No. 13/734,866, entitled "Steerable Medical Guide Wire Device," filed on Jan. 4, 2013, and U.S. patent application Ser. No. 11/898,475, entitled "Micro-steerable Catheter," filed on Sep. 17, 2007 disclose catheters and materials for various medical applications. The disclosures of these copending U.S. patent applications are hereby incorporated by reference in their entireties.

SUMMARY

According to one embodiment of the present invention, a remotely activated catheter includes an electromechanical polymer (EMP) actuator in the tip of the catheter that creates the required bending and motion, which steers the catheter through the vasculature. By controlling the bending and the motion, an operator can steer efficiently and accurately the catheter to a desired location within the body. In one embodiment, the EMP actuator may be embedded in the steerable tip at the distal end of the catheter. When activated, the EMP actuator bends the steerable tip through a controllable angle between 0° and 270°, thereby permitting the operator to steer the tip through the vasculature.

According to one embodiment of the present invention, a catheter assembly includes an elongated catheter shaft having a proximal end, a distal end, and an intermediate region between the distal end and the proximal end. The distal end includes a steerable tip that has embedded in it an electromechanical polymer (EMP) actuator, which is configured to cause the steerable tip to deform in response to an electrical control signal. The proximal end may include a power source that provides the electrical control signal. The catheter assembly may be equipped for use in various applications, such as tissue ablation, electrical mapping, stent delivery, embolics delivery, and guide wire steering. A control circuit may be provided at the proximal end of the catheter shaft, for controlling the electrical control signal from the power source. The control circuit therefore controls the deflection of the steerable tip. The electrical control signal may have an AC component modulated on a DC bias voltage.

According to one embodiment of the present invention, the catheter assembly may further include a storage medium for storing selectable predefined electrical control signals corresponding to predefined deflections, and an external interface for receiving selection information which enables the control circuit to select one of the predefined electrical control signals from the storage medium. In one implementation, the external interface allows a user to select by name one of many sets of control signals, with each set of control signals being signals calibrated for configuring the catheter assembly to mimic a known catheter. The selected set of control signals includes the selected preconfigured electrical control signal.

According to one embodiment of the present invention, one or more sensors provide sensor signals representative of environment conditions surrounding the steerable tip. The sensor signals are relayed back to the control circuit for processing. One or more EMP actuators acting as sensors may implement these sensors. In fact, some of the EMP actuators may act as both actuator and sensor. The control circuit processes the sensor signals to adjust the electrical control signal dynamically. In one embodiment, the sensors perform a pressure sensing function, and the deflection of the steerable tip is adjusted according to the sensed pressure to maintain a predetermined level of deflection.

According to one embodiment of the present invention, the steerable tip may include a relatively stiff region and a relatively flexible region. The EMP actuator is disposed in the stiff region so that, when activated, the EMP actuator bends the steerable tip toward the flexible region. Thus, a catheter tip of the present invention allows repeatable, fine and accurate articulation. Because the EMP actuator in the catheter tip may be activated to bend the catheter tip through any one of a wide range of angles, a single catheter may replace multiple conventional catheters that have been required in the prior art.

According to one embodiment of the invention, the distal portion of a catheter includes a steerable tip, which includes a relatively thin EMP actuator supported in a relatively stiff material. The steerable tip has two regions surrounding a lumen that are different in stiffness. A relatively stiff material forms that first region, which surrounds the relatively thin EMP actuator provided on one side of the lumen. A relatively flexible and soft material forms the second region, which is disposed on the other side of the lumen and at the distal portion of the steerable tip. The EMP actuator bends in response to an applied voltage. As the EMP actuator is embedded in the relatively stiff region, the steerable tip bends away from the stiff region and towards the flexible region.

According to another embodiment of the invention, the steerable tip includes longitudinal strips forming a relatively stiff region that is disposed on one side of the lumen. The rest of the steerable tip includes a relatively flexible material. An operator may vary the width or the number of strips in the relatively stiff region to control the angle or the direction of deflection in the steerable tip, thereby achieving steering.

According to yet another embodiment of the invention, the steerable tip includes a relatively stiff region provided by a helical or spiral strip disposed around the periphery of the steerable tip. The helical strip creates a flexible bending section that is both kink-resistant and having the ability to withstand a torque. The rest of the steerable tip includes a relatively flexible material.

According to still another embodiment of the invention, the steerable tip includes a relatively rigid main body in which an EMP actuator is disposed and a plurality of strips extending outwardly from the main body. When activated, the steerable tip bends towards the strips.

The present invention may be better understood upon consideration of the detailed description below in conjunction with the accompanying drawings.

BRIEF DESCRIPTION OF THE DRAWINGS

FIG. 1 shows catheter 10, which includes an electromechanical polymer (EMP) actuator-embedded steerable tip 16 at distal end 18, according to one embodiment of the present invention.

FIG. 2 shows catheter 10 of FIG. 1, with the EMP actuator activated to deflect steerable tip 16 through an acute angle.

FIG. 3 shows catheter 10 of FIG. 1, with the EMP actuator activated to deflect steerable tip 16 through an obtuse angle.

FIG. 4 shows steerable tip 16 at distal end 18 of catheter 10, according to one embodiment of the present invention.

FIG. 5 is a cross section of steerable tip 16 of FIG. 4, taken along line 5-5.

FIG. 6 shows steerable tip 16 at distal end 18 of catheter 10, according to a second embodiment of the present invention.

FIG. 7 is a cross section of steerable tip 16 of FIG. 6, taken along line 7-7.

FIG. 8 shows steerable tip 16 at distal end 18 of the catheter 10, according to a third embodiment of the present invention.

FIG. 9 is a cross section of steerable tip 16 of FIG. 8, taken along line 9-9.

FIG. 10 shows steerable tip 16 at distal end 18 of catheter 10, having a helical EMP actuator, according to a fourth embodiment of the present invention.

FIG. 11 is a cross section of steerable tip 16 of FIG. 10, taken along line 11-11.

FIG. 12 shows steerable tip 16 at distal end 18 of catheter 10, according to a fifth embodiment of the present invention.

FIG. 13 is a cross section of steerable tip 16 of FIG. 12, taken along line 13-13.

FIG. 15 shows EMP actuator 64 disposed in an intermediate section of body 22 of a catheter, in accordance with a seventh embodiment of the present invention.

FIGS. 16A, 16B, 16C and 16D are cross sections of the catheter of FIG. 15, taken along lines 16A-16A, 16B-16B, 16C-16C and 16D-16D, respectively.

FIG. 17 shows EMP actuators disposed in body 22 of a catheter, in accordance with an eighth embodiment of the present invention.

FIG. 18 is a cross section showing EMP actuators of FIG. 17, taken along line 18-18.

DETAILED DESCRIPTION OF THE PREFERRED EMBODIMENTS

Figure 14:
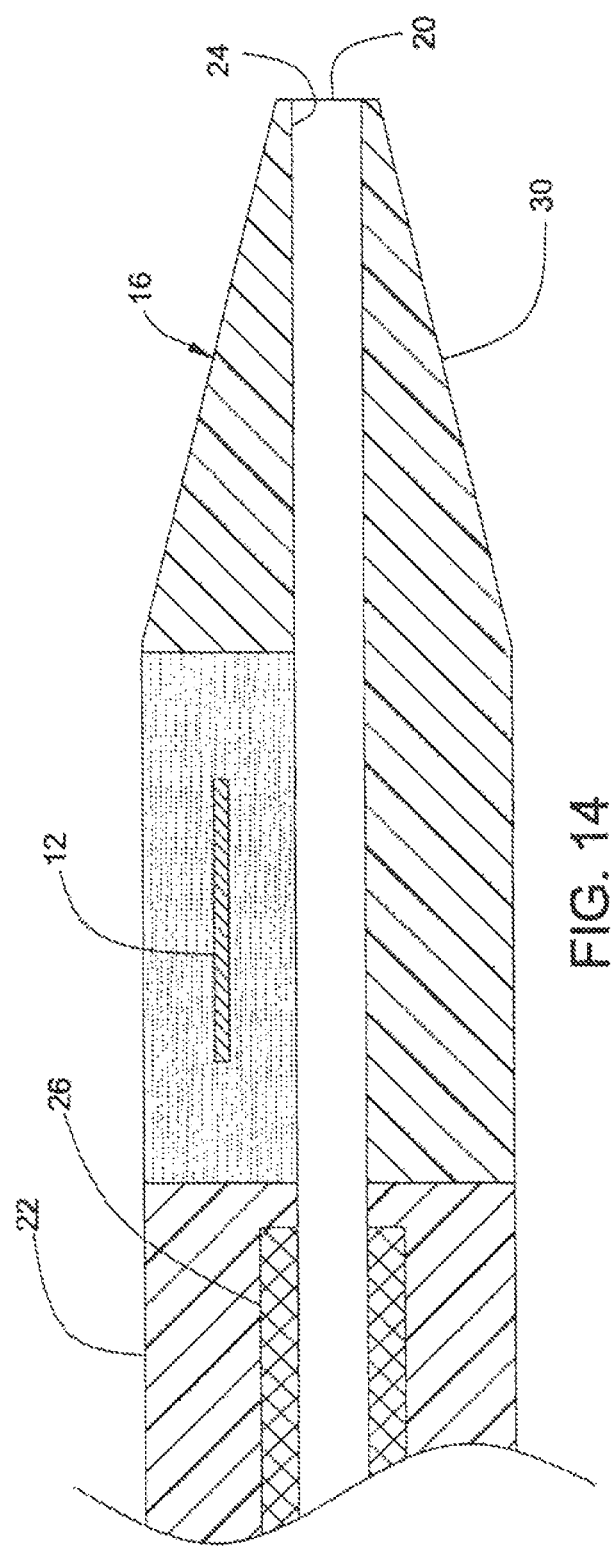
FIG. 14 shows EMP actuator 12 disposed in steerable tip 16, according to a sixth embodiment of the present invention.

This detailed description illustrates exemplary embodiments of the invention and does not limit the present invention. Many other embodiments of the invention may differ in detail from the embodiments described herein. The present invention is set forth in the appended claims.

According to one embodiment of the present invention, FIG. 1 shows catheter 10 having steerable tip 16 at distal end 18. Electromechanical polymer (EMP) actuator 12 (not shown in FIG. 1; see, e.g., FIGS. 5, 7, 9, 11, 13 and 14 herein) is provided inside steerable tip 16. EMP actuator 12 may include one or more polymer layers with electromechanical properties. Copending U.S. patent application ("EMP Actuator Application"), Ser. No. 13/683,963, entitled "Localized Multimodal Electromechanical Transducers," filed on Nov. 21, 2012, provides some examples of EMP actuators suitable for use in the present invention. The disclosure of the EMP Actuator Application is hereby incorporated by reference in its entirety to provide technical background information.

Electrical source 14 and controller 15 located at the proximal region 17 may provide an electrical activation signal to activate EMP actuator 12. The activation signal causes, in this embodiment, a mechanical response from EMP actuator 12 in the form of a deformation (e.g., bending, stretching, contracting, rotating or vibrating). A modulated sequence of electrical pulses in the activation signal varies the amount of deformation in EMP actuator 12. By embedding at least one EMP actuator 12 in catheter tip 16 at distal end 18 of catheter 10 and by judiciously selecting the durometer and shape of the material around the EMP actuator 12, the present invention allows fine and pre-defined articulation of steerable tip 16. The present invention permits an operator to steer steerable tip 16 of the catheter through the vasculature.

Catheter 10 includes lumen 20 for accommodating a guide wire. Although FIG. 1 shows EMP actuator 12 to be located at or near distal region 18 of catheter 10, EMP actuators 12 may also be disposed at other locations on catheter 10 to provide desired movements and articulations.

In one implementation, EMP actuator 12 may be modeled as a capacitor. In that embodiment, EMP actuator 12 includes an activated state, a charged inactive state, and a deactivated state. In the deactivated state, the terminals of the capacitor are grounded, so that EMP actuator 12 is not deformed or deflected. In the activated state, in response to an electrical current or a voltage applied to the electrodes of EMP actuator 12, EMP actuator 12 undergoes a volumetric change that causes the actuator to bend, deflect, or vibrate. By carefully selecting (i) the voltage applied to actuator 12, (ii) the shape and size of the actuator, (iii) the durometer, shape and size of the material surrounding EMP actuator 12, or (iv) any combination of these parameters, the deflection of EMP actuator 12—and hence steerable tip 16—may be controlled. FIGS. 1-3 illustrate deflecting steerable tip 16 from 0 degrees (FIG. 1) through an acute angle (FIG. 2) and an obtuse angle (FIG. 3). If EMP actuator 12 is disconnected or is isolated from the power source while in the activated state, EMP actuator 12 enters the charged inactive state in which EMP actuator 12 maintains the bending or deflection indefinitely. In this state, catheter 10 is fixed in the desired shape until the power source is reconnected and EMP actuator 12 enters the deactivated or activated state under active control.

Figure 21A:
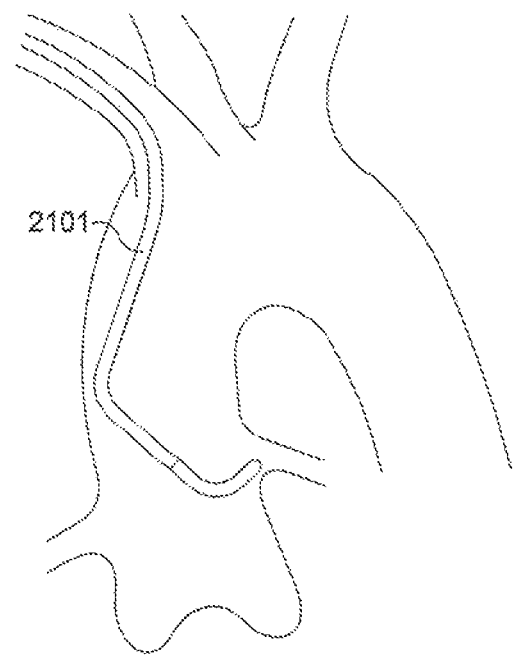
FIGS. 21(a) and 21(b) show catheters 2101 and 2102 required to access the left and right coronary arteries, respectively.
Figure 21B:
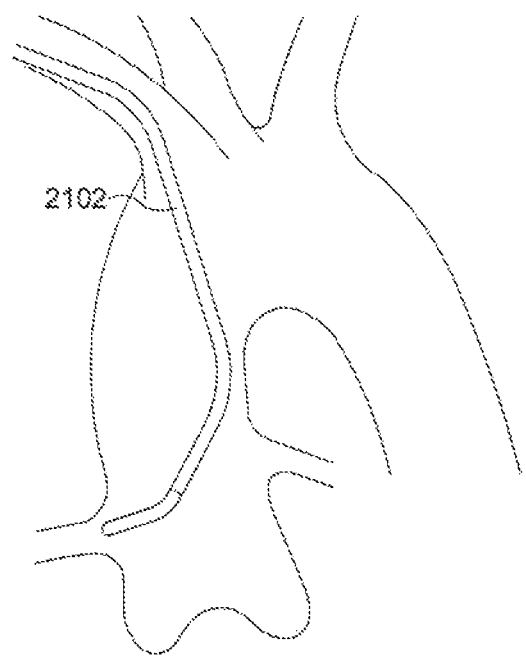

FIGS. 21(*a*) and 21(*b*) show catheters 2101 and 2102 required to access the left and right coronary arteries, respectively. As shown in FIGS. 21(*a*) and 21(*b*), catheters 2101 and 2102 are of different shapes because the different locations of the access points into the left and right coronary arteries. In the prior art, after achieving access to the intended artery, the catheter is retracted, while leaving the guide wire in place, so that a different catheter can then be substituted. It is often the case in the prior art that a number of catheters are used in order to reach the location where therapy is required. The ability to configure steerable tip 16 of catheter 10 electrically into different shapes, deflections or orientations as required provides a versatile catheter that helps to reduce or eliminate the need for changing catheters multiple times. To achieve this goal, according to one embodiment of the present invention, multiple EMP actuators positioned at predetermined locations in steerable tip 16 of catheter 10.

Figure 19A:
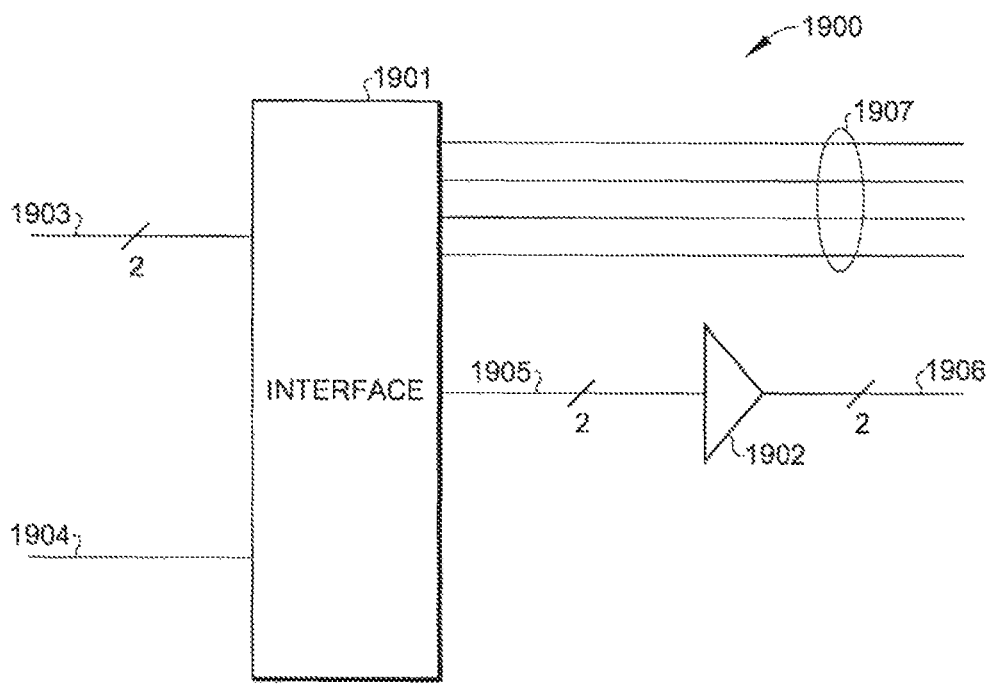
FIG. 19(a) shows schematic circuit 1900 in one implementation of controller 15, according to another embodiment of the present invention.
Figure 19B:
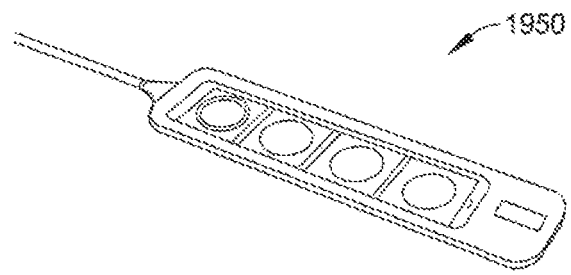
FIG. 19(b) shows user interface device 1950 having four selectable settings each corresponding to a pre-calibrated configuration of the catheter, in accordance with one embodiment of the present invention.

Controller 15 regulates the voltage applied to each EMP actuator in catheter 10. FIG. 19(*a*) shows schematic circuit 1900 in one implementation of controller 15, according to another embodiment of the present invention. As shown in FIG. 19(*a*), circuit 1900 receives selection signals 1903 and analog input signal 1904 at interface 1901. An external host computer, for example, may provide these signals. Selection signals 1903 in circuit 1900 is suitable for use in a catheter that has four EMP actuators. As shown in FIG. 19(*a*), selection signals 1903 may be a 2-bit bus that allows selection of any of the four EMP actuators. Interface 1901 decodes selection signals 1903 to provide enable signals 1907, which are each an enable signal to a corresponding one of the EMP actuators. Amplifier 1902 amplifies analog signals 1905, which are derived from analog input signal 1904, to provide analog signals 1906 at the appropriate operating voltages for use with the EMP actuators (e.g., 0-1500 volts). Circuit 1900 may also include power circuits (not shown) that provide the required supply voltages to amplifier 1902. In this implementation, each of enable signals 1907 may control a switch that conducts one of analog signals 1906 to the corresponding input terminals of the selected EMP actuator. A potentiometer (not shown) may allow manual fine adjustment of analog signal 1904. Such a fine adjustment further refines the desired shape or position of the steerable tip. As each EMP actuator is electrically a capacitor, the EMP actuator remains activated so long as the electrodes remain charged. Thus, in this embodiment, the external host computer may select the LIMP actuators one by one to provide the corresponding required voltages. Relaxation of each EMP actuator is achieved by discharging (e.g., applying a zero voltage) to an activated EMP actuator. Analog signal 1904 may include an AC component to enable vibrations. For example, analog signal 1904 may be an analog signal having an AC component modulated on a DC bias voltage. The DC bias voltage determines the deflection and the AC component provides the amplitude and frequency of vibration (e.g., 150-250 Hz). Available parameters to be set on analog signal 1904 include frequency, amplitude, and pulsing parameters. Predetermined sets of parameters may be provided for user selection based on the desired force to be applied.

In one embodiment, the host computer stores a number of pre-determined configurations each representing a particular combination of control voltages for the EMP actuators in the catheter. The host computer may provide a user interface for a user to select a particular combination to apply to the catheter over interface 1901 to achieve any of the pre-defined shapes, deflections or orientations. FIG. 19(*b*) shows user interface 1950 having 4 selectable settings each corresponding to a pre-calibrated configuration of the catheter, in accordance with one embodiment of the present invention. As shown in FIG. 19(*b*), a physician can select any of configurations "JR 4.0", "JL 4.0", "JR 3.5" and "JL 3.5." These configurations correspond to names of catheters well known to those of ordinary skill in the art. The names encode the shape (J), orientation (L or R) and the reach (3.5 or 4.0 cm) of the catheter. In this manner, an operator may easily select any of a number of pre-calibrated desired shapes, deflections or orientations as required by simply pressing a button, as the catheter is steered along the guide wire to the desired location in the vasculature. Accordingly, the numerous shapes, deflections or orientations required to steer the catheter to its final location are achieved without changing catheters. As a result, a safer and shorter procedure is achieved.

Figure 20:
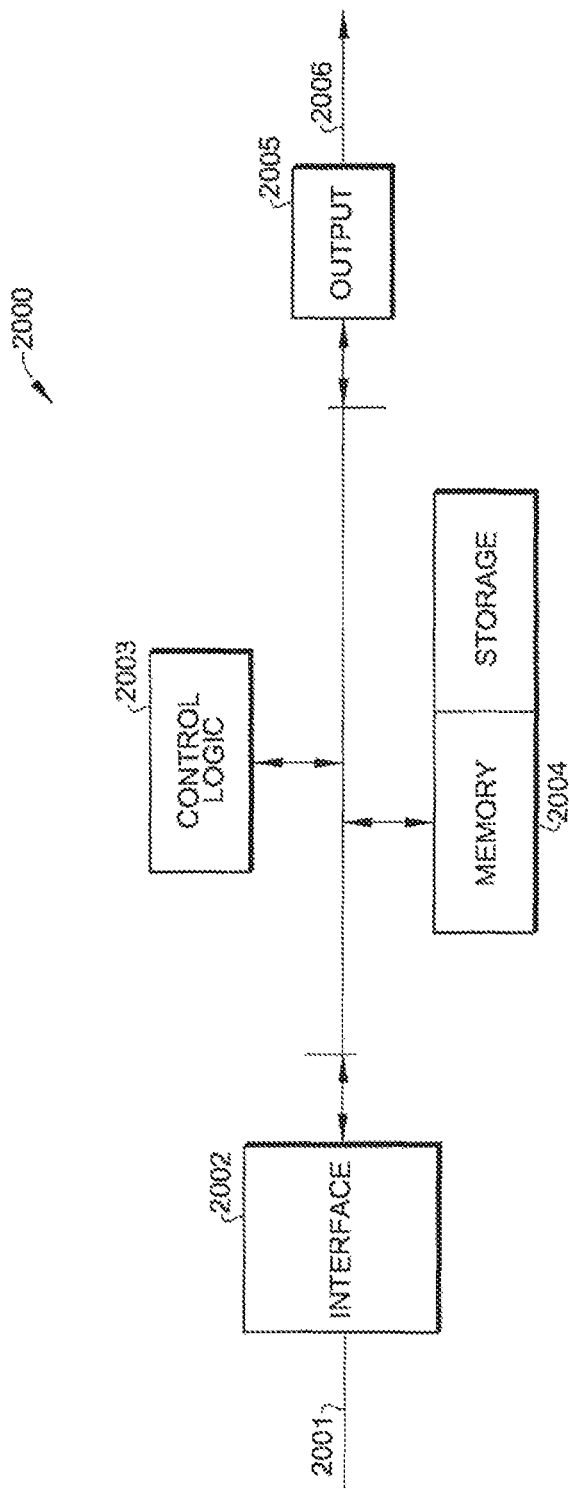
FIG. 20 shows schematic circuit 2000 in one implementation of controller 15, according to one embodiment of the present invention.

The settings that provide the pre-defined shapes, deflections or orientations at each actuator may be stored in controller 15. FIG. 20 shows schematic circuit 2000 in one implementation of controller 15, according to another embodiment of the present invention. As shown in FIG. 20, controller 15 includes interface 2002, which receives control signals from an external host computer over an industry standard bus 2001 (e.g., a USB connection). The control signals on bus 2001 may configure or program controller 15. Alternatively, the control signals on bus 2001 may be, for example, commands to controller 15 to output specific control signals to a specified EMP actuator. Specifically, controller 15 includes control logic circuit 2003 (e.g., a microprocessor), which may store into memory system 2004 configuration information that enables specific calibrated voltages to be applied to the EMP actuators to achieve specific pre-determined amounts of deflection or bending in that EMP actuator. Memory system 2004 may include a non-volatile portion for storing calibrated configuration information. Such calibrated configuration information may be programmed into the non-volatile portion of the memory during a manufacturing step, before catheter 10 is put to clinical use. Alternatively, a physician may store particular configurations that he or she finds particularly useful or used often.

When instructed by the external host computer through bus 2001, controller 15 may retrieve from memory system 2004 and may output the retrieved programmed voltage through output circuit 2005 on output bus 2006. In one implementation, the retrieved program voltage is encoded in a digital signal. A digital-to-analog converter circuit converts the digital signal to an analog voltage, which is then amplified in output circuit 2005. Output bus 2006 includes selection signals that specify the EMP actuator selected for activation, and the analog output signals that are applied to the EMP actuator to obtain a desired deflection angle, or any other suitable electromechanical response. By storing calibrated voltages, different predetermined electromechanical responses may be elicited from the EMP actuator, as needed. For example, the operator may select a particular deflection to allow the steerable tip to be steered into a particular branch of an artery. Thus, a catheter having a steerable tip of the present invention permits an operator to traverse the vascular system using a single catheter, or at least a very small number of catheters, without using frequent catheter changes, as required in certain applications.

As discussed in the EMP Actuator Application incorporated by reference above, an EMP actuator can also act as a sensor. This is because a mechanical force imposed across the charged EMP actuator results in an electrical response. Thus, an EMP actuator (e.g., in its charged inactive state) can also act as a sensor in the body, such a pressure sensor. These sensors may relay sensing signals representative of the conditions at the distal end of the catheter back to a processor (e.g., controller 15) for processing. A catheter integrating both EMP actuators and EMP actuators acting as sensors thus includes an automatic closed-loop, dynamic compensation mechanism to maintain a desired combination of deflection and pressure.

FIGS. 4 and 5 illustrate catheter 10, according to a first embodiment of the invention. Catheter 10 has steerable catheter tip 16, intermediate portion 22, and lumen 20 that extends through the axial length of catheter 10. Lumen 20 is surrounded by thin liner 24, which may be, for example, a one-mil thick PTFE material. Intermediate portion 22 includes braided segment 26 which reinforces liner 24, providing rigidity and support for lumen 20, thus preventing lumen 20 from collapsing. The length of intermediate portion 22 depends upon the type and application of catheter 10, but may be up to about 100 cm long.

Intermediate portion 22 and steerable tip 16 may be formed integral to each other. Alternatively, steerable tip 16 and intermediate portion 22 may be separately formed and are attached to each other subsequently. As shown in FIG. 4, EMP actuator 12 is embedded in one portion of steerable tip 16 and does not extend fully circumferentially around lumen 20. Thus, EMP actuator 12 is seen only in an "upper" portion of FIG. 5. In the activated state, the portion containing EMP actuator 12 bends toward the non-EMP actuator-containing portion of steerable tip 16.

By controlling the durometer and shape of the materials forming steerable tip 16, the amount of deflection and orientation therein may be varied. As shown in FIG. 5, the portion containing EMP actuator 12 in steerable tip 16 is relatively stiffer than the rest of the steerable tip 16. As EMP actuator 12 is a thin, relatively fragile device (e.g., typically about 0.015 inches thick), EMP actuator 12 may be encapsulated in a relatively stiff urethane, for example. A suitable urethane may have, for example, a durometer of about 75 A for support and protection of EMP actuator 12. As shown in FIG. 5, EMP actuator 12 may be embedded in a relatively soft or flexible material 28 to provide strain relief. Strain relief material 28 may be, for example, a urethane having a durometer of about 25 A.

EMP actuator 12 and strain relief material 28 are encapsulated in a relatively soft and flexible material 30, such as a urethane having a durometer of about 5 A. Material 30 includes a radio-plaque filler (e.g., barium sulfate) to allow tracking by X-ray radiation of the location of steerable tip 16, as catheter 10 is being threaded through the body's vasculature.

As shown in FIG. 5, section 32, which is formed out of a relatively stiff material to provide rigidity and strength to steerable tip 16, is disposed at the periphery of steerable tip 16 where steerable tip 16 joins intermediate region 22. The relatively stiff material of section 32 may be, for example, a urethane material having a durometer of 75 A Shore.

Thus, the present invention permits an operator finer, safer and more accurate articulation of steerable tip 16 than are available in conventional catheters using guide wires by controlling the voltage applied to EMP actuator 12 in the activated state and selecting the durometer and shape of the material that surrounds EMP actuator 12 and steerable tip 16. According to the embodiment illustrated in FIG. 5, steerable tip 16 may have a durometer of 5A Shore to allow a deflection angle ($\theta$) of 180 degrees or more. When steerable tip 16 has a durometer of about 75 A Shore, the deflection angle ($\theta$) is limited to about 10 degrees. Thus, as the operator pushes steerable tip 16 through a blood vessel, for example, the operator may make fine adjustments of the deflection angle and the orientation of steerable tip 16 and other portions of catheter 10. Accordingly, the operator may aim steerable tip 16 with a high degree of precision through tortuous paths of the vasculature system.

FIGS. 6 and 7 illustrate catheter 10, according to a second embodiment of the invention. As discussed above, distal portion 18 of catheter 10 includes steerable tip 16. As shown in FIG. 7, relatively thin and fragile EMP actuator 12 is disposed around lumen 20 in relatively flexible strain-relief material 28. Steerable tip 16 includes a relatively flexible and soft material in region 30 and a relatively stiff material in region 32 that surrounds EMP actuator 12. As shown in FIGS. 6 and 7, region 32 occupies an "upper" portion of steerable tip 16. Region 32 may be made out of a urethane material having a durometer of 75 A Shore. A suitable material for region 30 may be, for example, a urethane having a durometer of 5 A Shore.

When activated (i.e., a voltage being applied) EMP actuator 12 bends towards the more flexible and soft material of region 30 (i.e., "downwards" in FIG. 7), as EMP actuator 12 is embedded in the relatively stiff region 32.

FIGS. 8 and 9 illustrate catheter 10, in accordance with a third embodiment of the present invention. As in the embodiments illustrated in FIGS. 4-7, discussed above, catheter 10 includes EMP actuator 12 disposed in relatively flexible strain-relief section 28 adjacent lumen 20. Steerable tip 16 includes relatively stiff longitudinal strips 36 disposed on one side of the lumen 20 (i.e., the "upper" portion in FIG. 9). Relatively flexible region 38 forms the rest of steerable tip 16. When EMP actuator 12 is activated, the widths and the number of strips 36 control both the amount of deflection and the direction of deflection, bending steerable tip 16 towards relatively flexible region 38.

FIGS. 10 and 11 illustrate catheter 10, in accordance with a fourth embodiment of the invention. As in the embodiments illustrated in FIGS. 4-9, discussed above, catheter 10 includes EMP actuator 12 disposed in relatively flexible strain-relief section 28 adjacent lumen 20. As shown in FIG. 10, steerable tip 16 includes relatively stiff region 40 in a helical or spiral strip disposed around the periphery of steerable tip 16. Relatively stiff helical strip 40 creates a flexible bending section that is also kink-resistant and torque-providing. Relatively flexible material in portion 42 forms the remainder of steerable tip 16. When activated, EMP actuator 12 bends in response to an applied voltage. Although illustrated in FIGS. 10-11 as having a single helix strip (i.e., helical strip 40), steerable tip 16 may have two or more helical strips to achieve the desired articulations.

FIGS. 12 and 13 illustrate catheter 10, in accordance with a fifth embodiment of the present invention. As in the embodiments illustrated in FIGS. 4-11, discussed above, catheter 10 includes EMP actuator 12 disposed in relatively flexible strain-relief section 28 adjacent lumen 20. Relatively rigid portion 50 of steerable tip 16 includes main body 51 and strips 52 extending outwardly from main body 51. FIG. 13 shows rigid portion 50 to include four strips 52 extending in a "downward" manner. When activated, EMP actuator 12 bends steerable tip 16 towards strips 52 (i.e. "downward" in FIG. 13).

FIGS. 15 and 16 disclose catheter 10, in accordance with a seventh embodiment of the present invention. According to this embodiment, EMP actuator 64 is disposed in catheter body 22. Steering control of catheter body 22 may be achieved by varying the length and the shape of EMP actuator 64. As shown in FIG. 15, EMP actuator 64 may be provided in the form of a helical or curved strip. When inactive, catheter body 22 is relatively straight. When activated, catheter body 22 bends in a direction controlled by the shape of EMP actuator 64. Precise control of bending directions and deflection angles of catheter body 22 can be achieved by varying the voltage applied, the length and the size of EMP actuators 64, and its precise placement along catheter body 22.

Unlike the embodiments illustrated in FIGS. 4-16 and discussed above, in which the EMP actuators are placed adjacent lumen 20, EMP actuator 12 of steerable tip 16 in FIG. 14 is embedded in a relatively rigid region and is spaced from lumen 20. Relative soft and flexible region 30 form the rest of steerable tip 16. When activated, EMP actuator 12 bends steerable tip 16 towards strips 30 (i.e. "downward" in FIG. 14).

Although the embodiments illustrated by FIGS. 4-14 and discussed above each show single EMP actuator 12 of steerable tip 16 disposed at distal end 18 of catheter 10, additional EMP actuators may be disposed along the length of catheter 10 anywhere steering control is desired. Thus, according to the principles discussed above, when activated, these additions EMP actuators cause catheter 10 to bend in the desired directions. Referring to FIGS. 17 and 18, for example, catheter 10 includes EMP actuators 60 and 62 disposed in the body (i.e., intermediate region 22) of catheter 10. EMP actuators 60 and 62 are adjacent to each other, but offset at a predetermined angle relative to each other. Thus, an operator may actuate either one or both of EMP actuators 60 and 62 to control the bending and orientation of catheter body 22. For example, when both EMP actuators are in inactive, catheter body 22 is relatively straight. When only EMP actuator 60 is activated, catheter body 22 bends in a direction indicated generally by arrow A of FIG. 18. When only EMP actuator 62 is activated, catheter body 22 bends in a direction indicated generally by arrow B of FIG. 18. When both EMP actuators 60 and 62 are activated, catheter 10 bends in a direction indicated generally by arrow C of FIG. 18. Precise control of bending directions and deflection angles of catheter body 22 may be achieved by varying the sizes of EMP actuators 60 and 62, the relative angle between EMP actuators 60 and 62, and the material of catheter body 22.

Although the embodiments of the present invention discussed above all include a lumen in the catheter to accommodate a guide wire, having such a lumen is not necessary. A catheter may have, in some instances, more than one lumen or may not have a continuous lumen at all. If a catheter has no lumen, the catheter may be used for such functionality as tissue ablation. If the catheter is shrunk or scaled down to the size of a guide wire, the catheter itself is its own guide wire, and there is no need to provide the lumen. The catheters of the present invention may be customized for such applications as tissue ablation, electrical mapping, stent delivery, embolics delivery, or guide wire steering. Catheters of the present invention may be equipped to perform these functions in the same manner as conventional catheters. In some applications, e.g., mechanical tissue removal, the EMP actuators may be stimulated using control signals with an AC component (e.g., 150-250 Hz).

We claim:

1. A catheter assembly comprising:
an elongated catheter shaft having a proximal end, a distal end, and an intermediate region between the distal end and the proximal end;
a control circuit coupled to a power source at the proximal end of the elongated catheter shaft, wherein the control circuit is configured to control one or more electrical control signals from the power source; and
a steerable tip coupled to the distal end of the elongated catheter shaft, the steerable tip having one or more electromechanical polymer (EMP) actuators embedded therein, the one or more EMP actuators configured to cause the steerable tip to deform in response to the one or more electrical control signals, wherein at least one of the one or more EMP actuators acts as both an actuator and a sensor that detects environment conditions surrounding the steerable tip and provides sensor signals to the control circuit indicative of the environment conditions, wherein the control circuit adjusts the one or more electrical control signals in response to the sensor signals, and wherein the power source is configured to provide the one or more electrical control signals to one or more of the EMP actuators.

2. The catheter assembly of claim 1, further comprising:
an external interface configured to receive a selection of one or more of the electrical control signals, each of the electrical control signals being signals calibrated to cause the steerable tip to deform in a predetermined manner.

3. The catheter assembly of claim 1, wherein the one or more EMP actuators are further configured to:
detect pressure surrounding the steerable tip, wherein the steerable tip is deformed to maintain a predetermined deflection level based at least in part on the pressure detected.

4. The catheter assembly of claim 2, wherein the elongated catheter shaft further comprises a lumen for accommodating a guide wire.

5. The catheter assembly of claim 4, wherein the steerable tip comprises a first region and a second region that is flexible relative to the first region, such that the steerable tip deforms in a direction of the second region in response to one or more of the one or more electrical control signals.

6. The catheter assembly of claim 5, wherein the first region is adjacent a first portion of the lumen, and the second region is adjacent a second portion of the lumen, and wherein the one or more EMP actuators are located in a portion of the steerable tip that is adjacent to the intermediate region.

7. The catheter assembly of claim 4, further comprising a strain-relief region embedding the one or more EMP actuators and surrounding the lumen.

8. The catheter assembly of claim 1, wherein the intermediate region of the catheter shaft comprises an additional EMP actuator disposed in the intermediate region and comprising a helical EMP strip provided along a peripheral region.

9. The catheter assembly of claim 1, wherein the intermediate region further comprises two additional EMP actuators disposed in the intermediate region wherein the two additional EMP actuators are offset by a predetermined angle.

10. A method for providing a catheter assembly, comprising:
providing an elongated catheter shaft having a proximal end, a distal end, an intermediate region between the distal end and the proximal end, and in the distal end of the elongated catheter shaft, a steerable tip that has one or more electromechanical polymer (EMP) actuators embedded therein;
causing a deflection in the steerable tip, using the one or more EMP actuators, in response to one or more electrical control signals, wherein at least one of the one or more EMP actuators acts as both an actuator and a sensor that detects environment conditions surrounding the steerable tip, and wherein deflection of the steerable tip is based at least in part on the environment conditions; and
providing, using a power source in the proximal end, one or more of the one or more electrical control signals.

11. The method of claim 10, further comprising:
controlling, using a control circuit coupled to the power source in the proximal end, one or more of the one or more electrical control signals.

12. The method of claim 11, further comprising:
receiving, using an external interface, a selection of one of one or more of the one or more electrical control signals, each of the one or more of the electrical control signals being signals calibrated to cause the steerable tip to deform in a predetermined manner.

13. The method of claim 10, further comprising:
detecting pressure surrounding the steerable tip, using the one or more EMP actuators, wherein the deflection in the steerable tip is adjusted to maintain a predetermined deflection level based at least in part on the pressure detected.

* * * * *